(12) United States Patent
Nobles

(10) Patent No.: US 9,345,820 B2
(45) Date of Patent: May 24, 2016

(54) SUCTION CANISTER COVER

(71) Applicant: Jacqueline D. Nobles, Boynton Beach, FL (US)

(72) Inventor: Jacqueline D. Nobles, Boynton Beach, FL (US)

(73) Assignee: Jacqueline D. Nobles, Boynton Beach, FL (US)

( * ) Notice: Subject to any disclaimer, the term of this patent is extended or adjusted under 35 U.S.C. 154(b) by 0 days.

(21) Appl. No.: 14/592,497

(22) Filed: Jan. 8, 2015

(65) Prior Publication Data
US 2015/0190557 A1 Jul. 9, 2015

Related U.S. Application Data

(60) Provisional application No. 61/924,801, filed on Jan. 8, 2014.

(51) Int. Cl.
*A61M 1/00* (2006.01)
*B65D 81/38* (2006.01)

(52) U.S. Cl.
CPC ......... *A61M 1/0001* (2013.01); *B65D 81/3876* (2013.01)

(58) Field of Classification Search
CPC .... A61M 1/0001; A61M 27/00; B65D 25/26; B65D 25/54; B65D 81/3876; B65D 11/20; A61J 1/165; A61J 1/16
USPC ........... 220/737, 739, 663, 662, 592.17, 903; 229/403, 400
See application file for complete search history.

(56) References Cited

U.S. PATENT DOCUMENTS

| 4,193,525 A * | 3/1980 | Sommers | B65D 81/3886 206/430 |
| 2011/0114657 A1* | 5/2011 | Nygaard | B65D 23/12 220/738 |
| 2014/0048551 A1* | 2/2014 | Slipe, Sr. | B65D 81/3879 220/739 |

* cited by examiner

*Primary Examiner* — Robert J Hicks

(57) ABSTRACT

A suction canister cover is intended to hide the contents of a suction canister during a medical procedure from patients and other non-medical personnel who may become queasy at the sight of bodily fluids. The suction canister cover includes a base cover, a tubular lateral cover, an annular restraint, and a viewport. The base cover hides the bottom of the suction canister while the tubular lateral cover obscures the patients view through the sides of the suction canister. The annular restraint secures the suction canister cover to the suction canister to prevent the suction canister cover from being easily removed or sliding from the suction canister. The viewport allows medical personnel to view the volume of contents within the suction canister while keeping the contents blocked from patients and non-medical personnel.

18 Claims, 7 Drawing Sheets

SUCTION CANISTER COVER

The current application claims a priority to the U.S. Provisional Patent application Ser. No. 61/924,801 filed on Jan. 8, 2014.

FIELD OF THE INVENTION

The present invention relates generally to a cover for suction canisters to be used within the medical field. More specifically, the present invention relates to a suction canister cover that allows the user to view the volume of contents while hiding the contents from the patient.

BACKGROUND OF THE INVENTION

Suction canisters are used to contain the contents from respiratory secretions from the nasal, oral, or tracheotomy passages, as well as, gastric contents during a nasal gastric lavage. To medical professionals, viewing the excretions, bile, and other bodily fluids of patients is an everyday occurrence; however, to patients and other people who may not be medical professionals may become nauseous or queasy at the sight of such fluids. Currently, the medical professional needs to ask the patient to cover their eyes, go behind the patient, or turn their back to the patient in order to fill the suction canister to prevent the patient from becoming nauseous at the sight of seeing the bodily fluids.

Therefore, it is an object of the present invention to cover a suction canister and obscure the contents held within. A suction canister is inserted into the present invention in order to conceal the suctioned contents. The present invention includes an elastic annular restraint which secures the present invention onto the suction container to retain the obscurity of the contents while handling and transporting the suction canister. A viewport is included such that medical personnel are able to monitor the volume of the fluids filling the suction canister, while keeping the contents obscured from a patient.

DETAIL DESCRIPTIONS OF THE INVENTION

Figure 1:
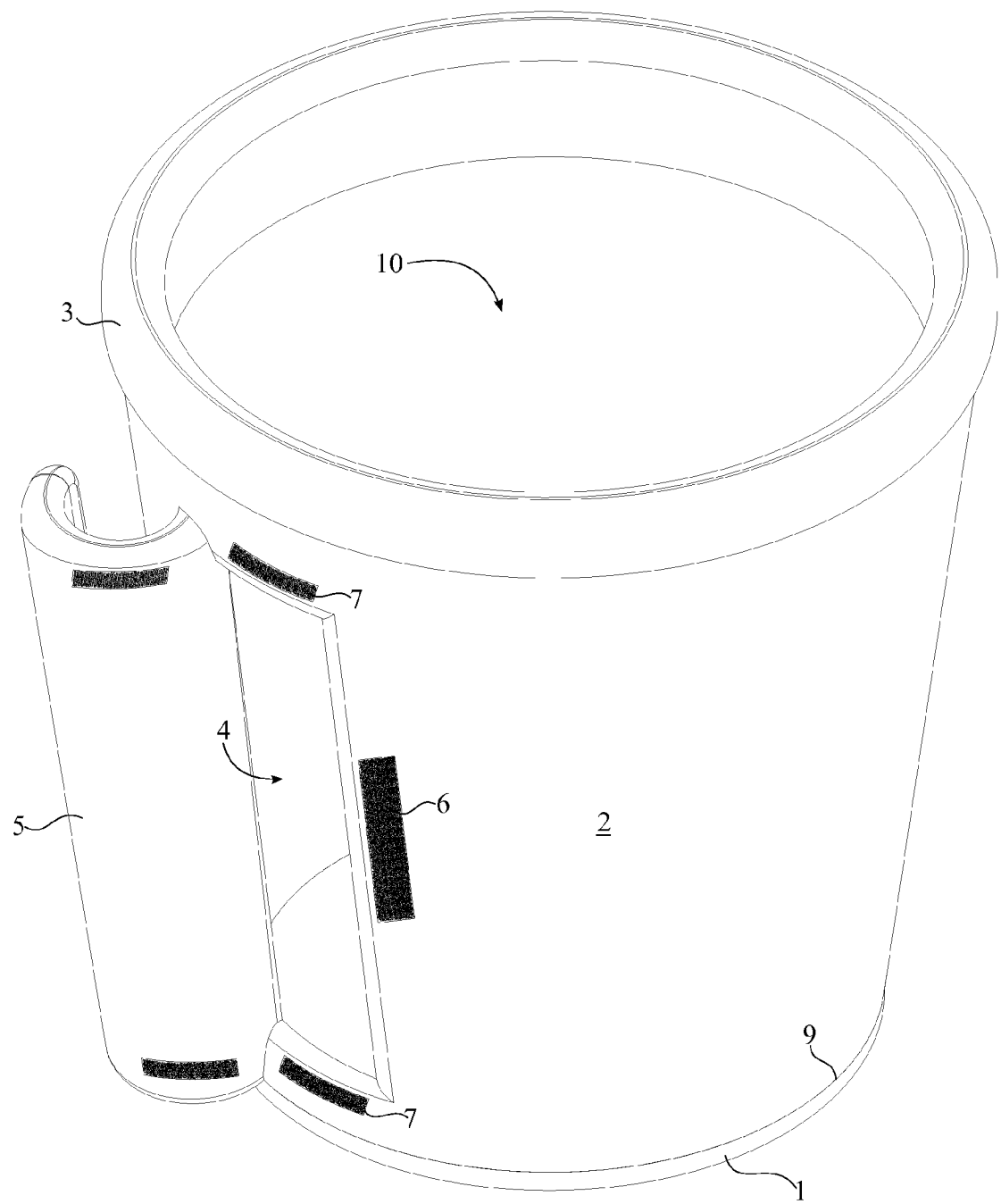
FIG. 1 is a top perspective view of the present invention.

All illustrations of the drawings are for the purpose of describing selected versions of the present invention and are not intended to limit the scope of the present invention.

The present invention is for a suction canister cover. A user, most likely a medical professional, of the present invention obscures the contents of a suction canister from others, to prevent a patient from becoming queasy or nauseous at the sight of the contents filling the suction canister. The user is still able to view the volume of the contents while obscuring the contents from others.

In accordance to FIG. 1 to FIG. 4, the present invention comprises a base cover 1, a tubular lateral cover 2, an annular restraint 3, and a viewport 4. The base cover 1 conceals a bottom portion of the suction canister. Similarly, the tubular lateral cover 2 conceals a lateral portion of the suction canister. The annular restraint 3 secures the present invention onto the suction canister under a lip of the suction canister. The viewport 4 allows the user to monitor the volume of contents within the suction canister during implementation of the present invention. The tubular lateral cover 2 comprises an annular base edge 9 and a suction canister receiving opening 10. The annular base edge 9 is positioned opposite the suction canister receiving opening 10 along the tubular lateral cover 2. The base cover 1 is perimetrically connected to the annular base edge 9 in order to provide a stable base support when the present invention is implemented around the suction canister. The suction canister is inserted into the present invention through the suction canister receiving opening 10 during the intended use of the present invention. The present invention is secured to the suction canister by the annular restraint 3, which is mounted onto the tubular lateral cover 2 about the suction canister opening 10. In the preferred embodiment, the annular restraint 3 is preferred to be an elastic band. In some other embodiments the annular restraint 3 can be but is not limited to a looped cord with an adjustable restraint, a semi-permanent adhesive or similar means to secure the present invention onto the suction canister and the tubular lateral cover 2 is tapered, in order to conform to the shape of the suction canister.

The viewport 4 traverses through the tubular lateral cover 2 between the annular restraint 3 and the base cover 1, which allows the user to view the height of the content within the suction container and, thus, allows the user to determine the volume of the content within the suction canister. Further in accordance to the preferred embodiment, the present invention comprises a viewport flap 5. The viewport flap 5 allows the user to cover the viewport 4 to completely conceal the suction canister. The viewport flap 5 is hingedly connected to the tubular lateral cover 2, adjacent to the viewport 4. The hinged connection allows the user to fold back the viewport flap 5 to assess the volume of fluid and subsequently conceal the suction canister by positioning the viewport flap 5 over the viewport 4.

Figure 2:
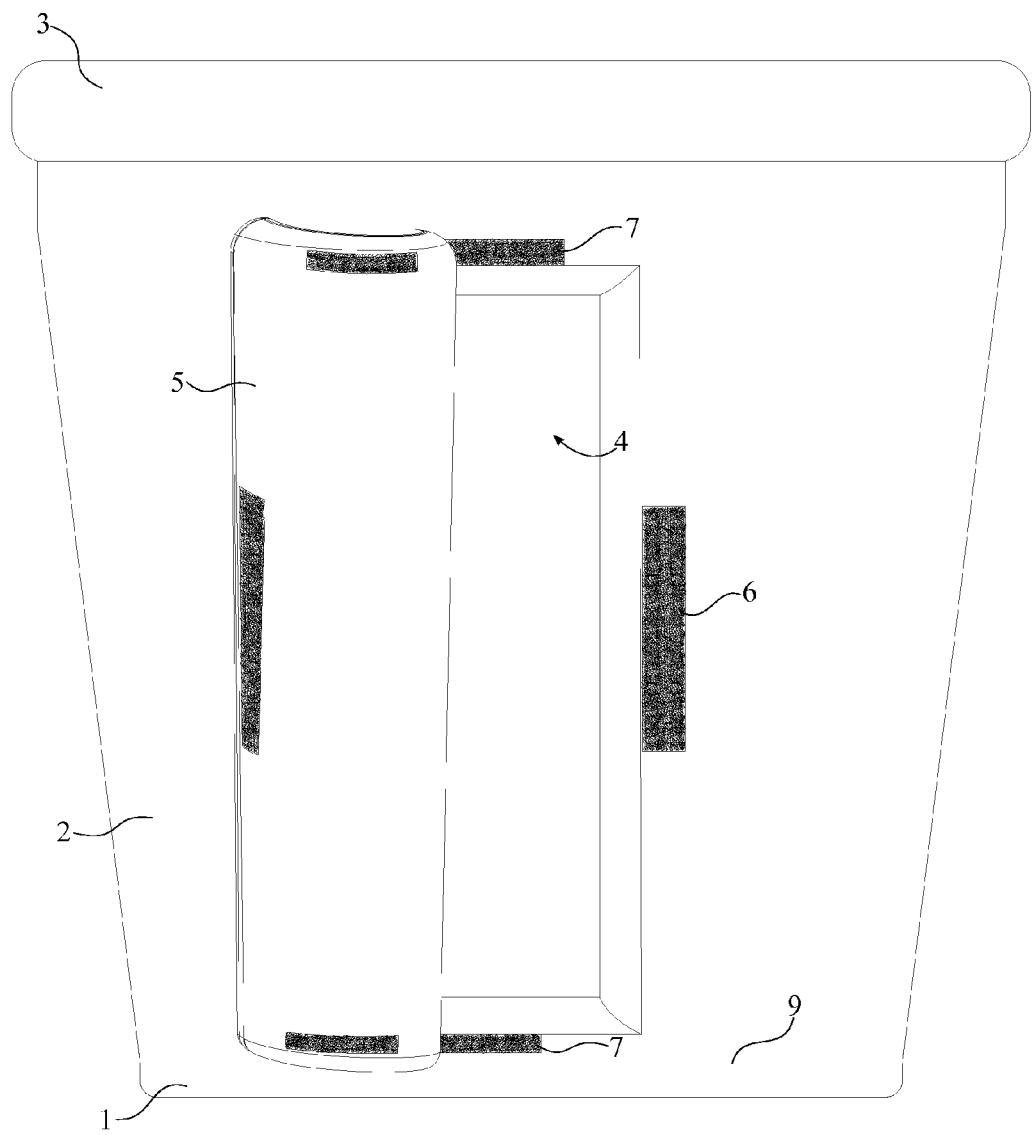
FIG. 2 is front view of the present invention.
Figure 3:
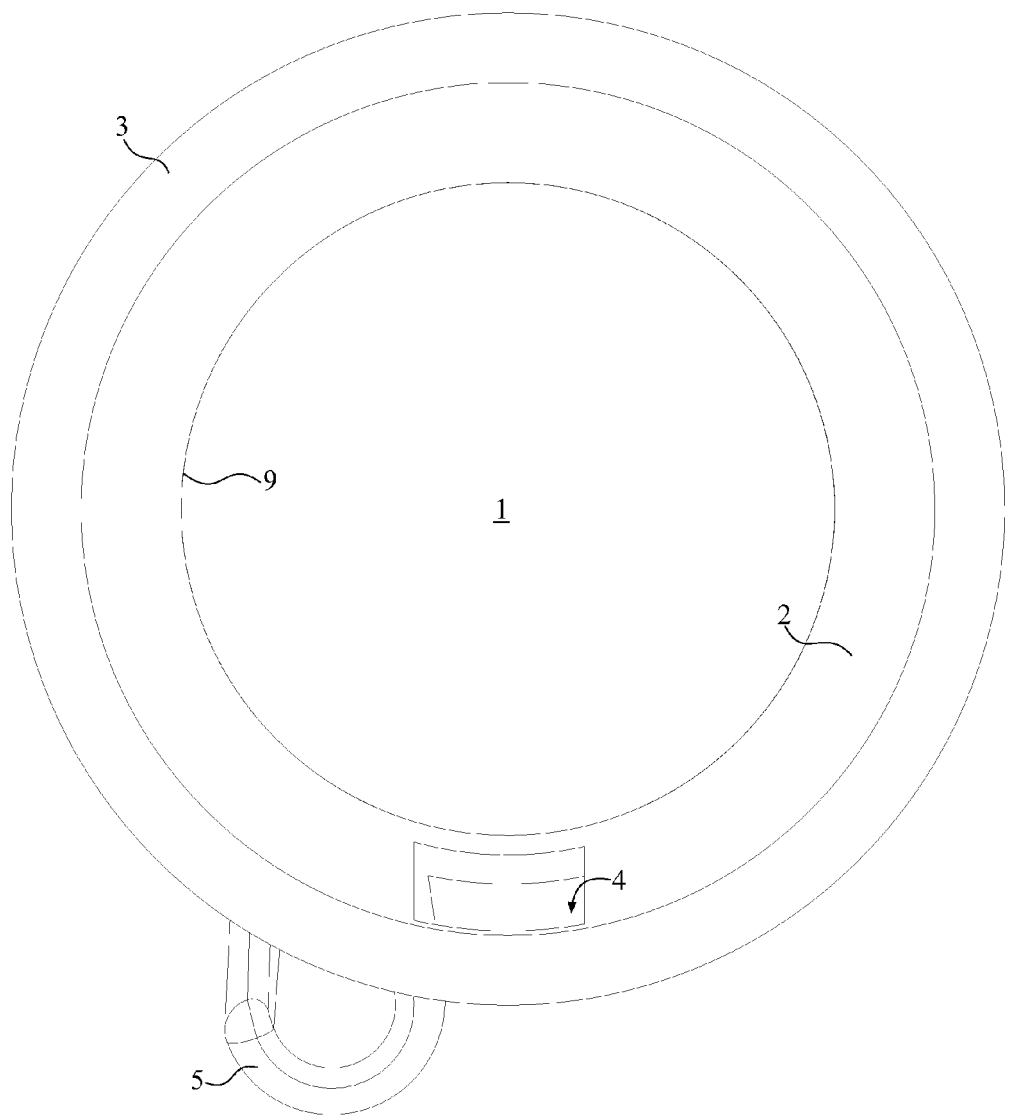
FIG. 3 is a top view of the present invention.
Figure 4:
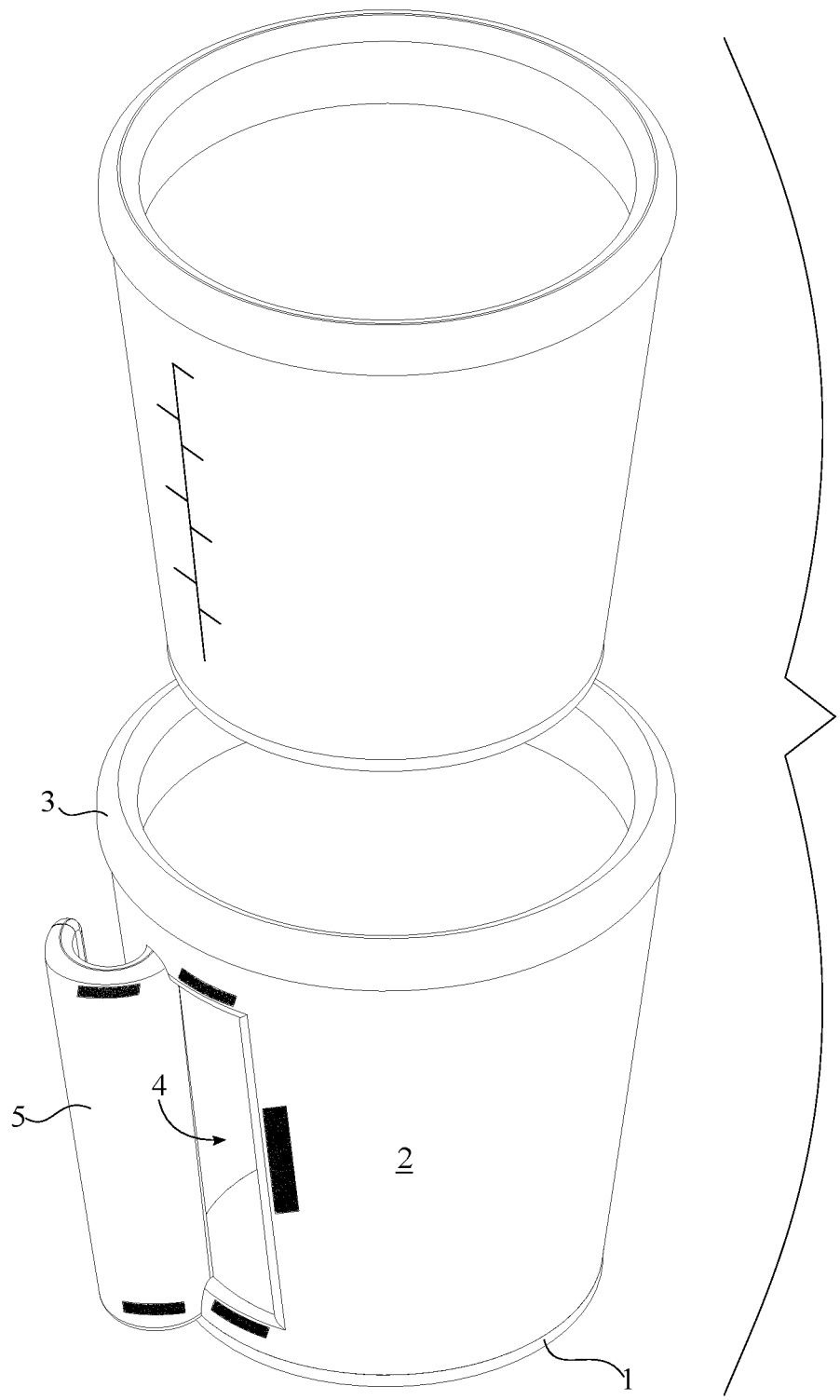
FIG. 4 is an exploded view of the present invention with a suction canister.
Figure 5:
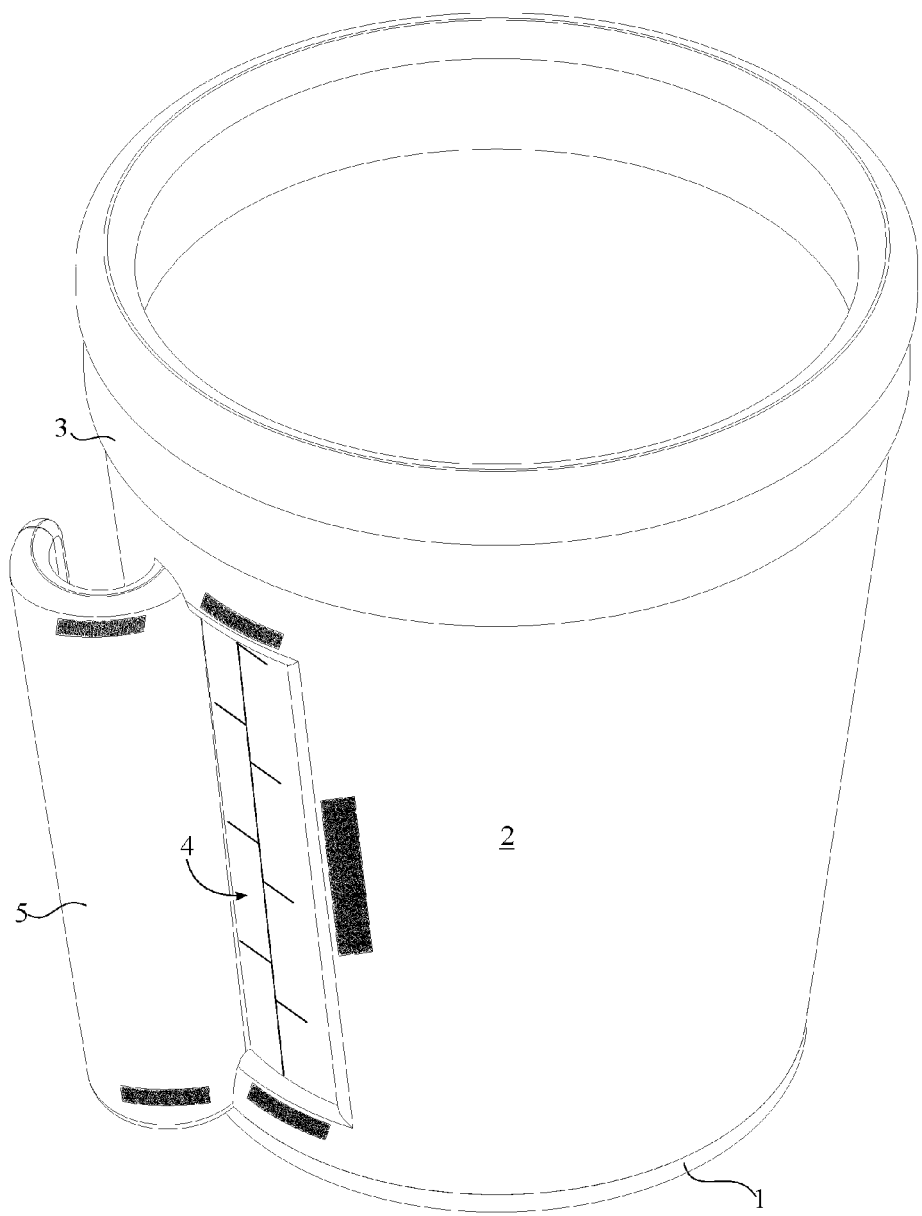
FIG. 5 is an perspective view of the suction canister positioned within the present invention.
Figure 6:
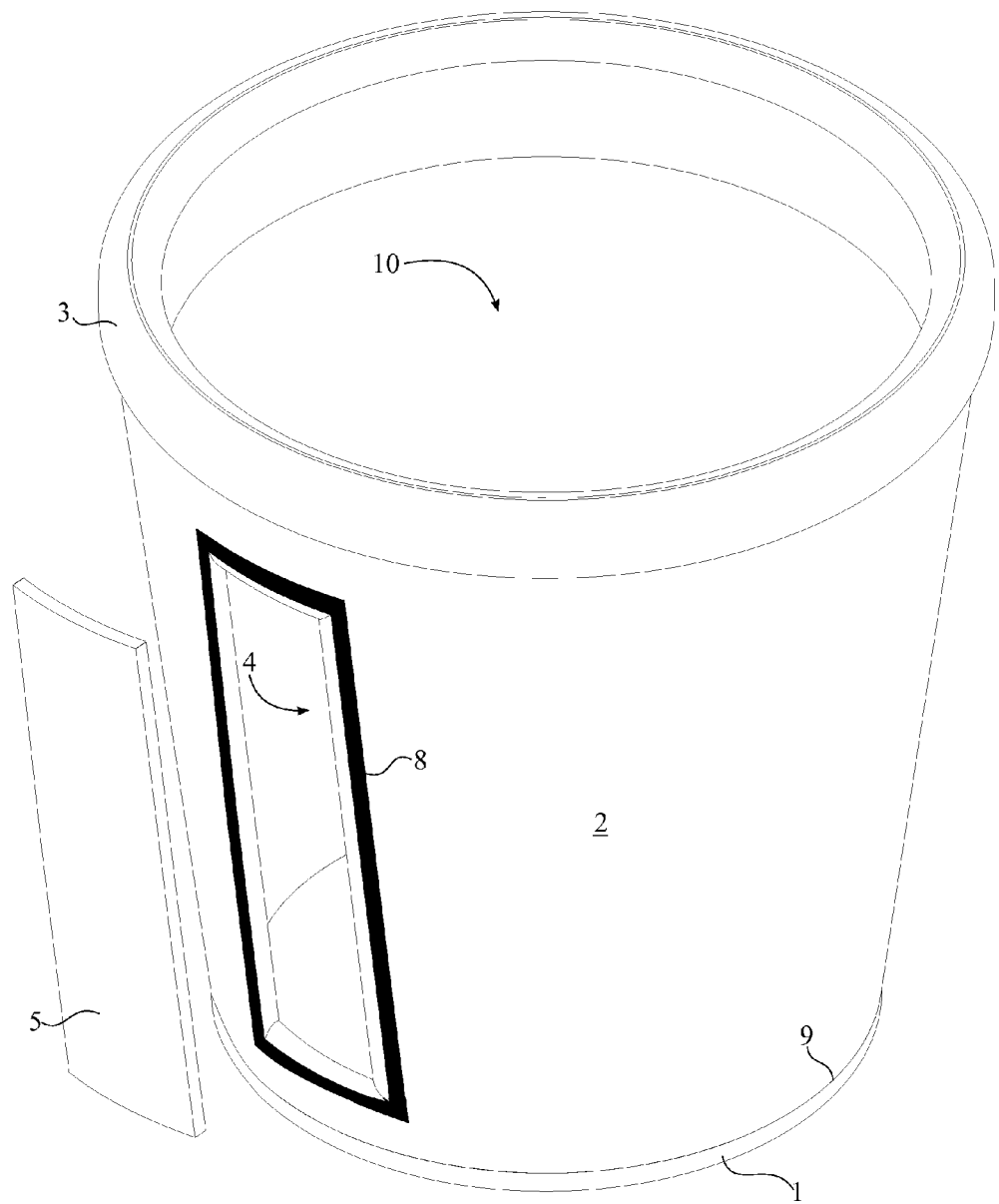
FIG. 6 is a top perspective view of an alternate embodiment for the present invention where the viewport flap is removable.
Figure 7:
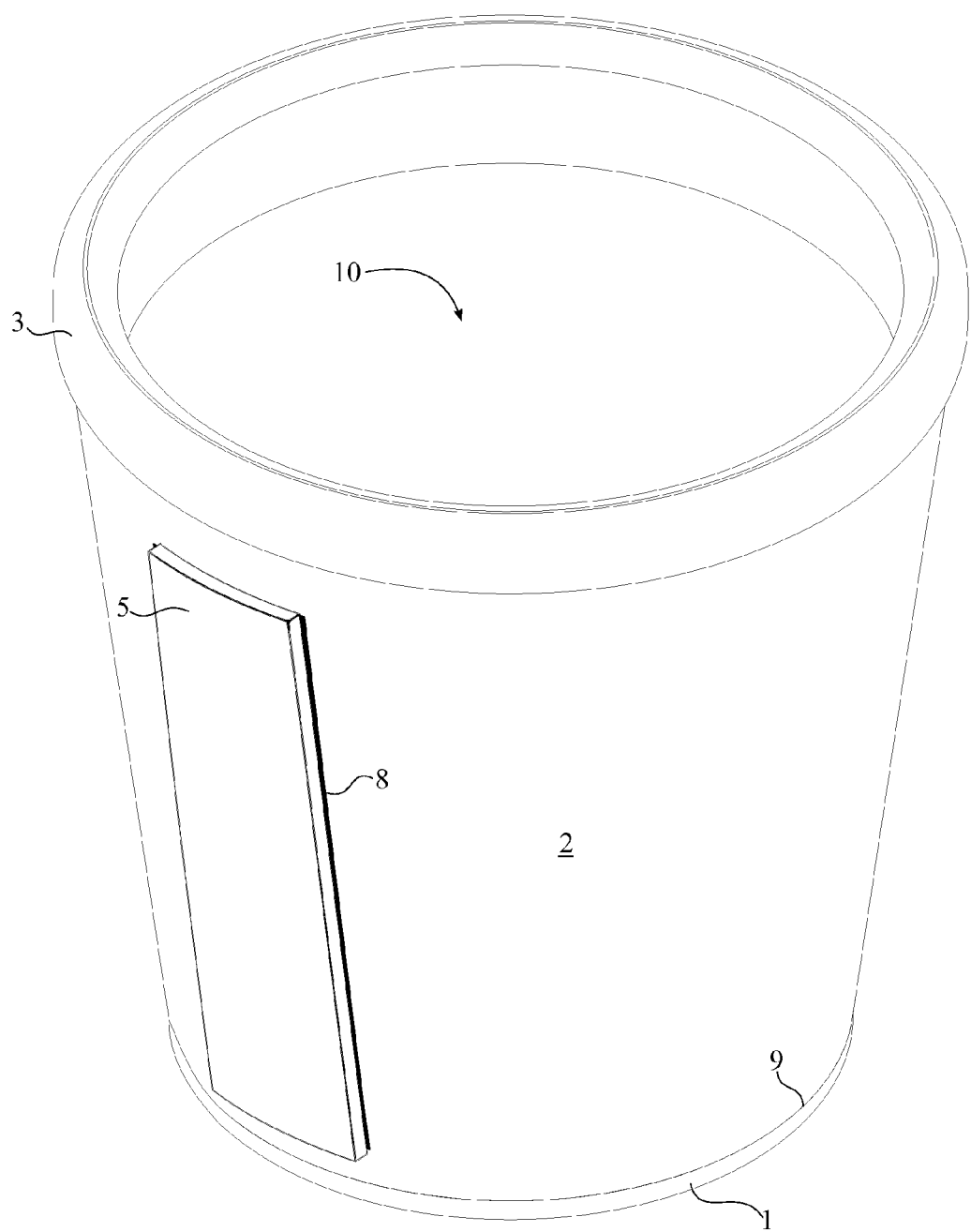
FIG. 7 is a top perspective view of an alternate embodiment for the present invention where the viewport flap is attached to the tubular lateral cover.

The preferred embodiment, depicted in FIG. 1 to FIG. 3, further comprises a primary flap fastener 6 and a pair of secondary flap fasteners 7. The primary flap fastener 6 and the pair of secondary flap fasteners 7 secure the viewport flap 5 onto the tubular lateral cover 2 when the viewport flap 5 is positioned across the viewport 4. The primary flap fastener 6 is mounted onto the tubular lateral cover 2 adjacent to the viewport 4. The primary flap fastener 6 is positioned opposite to the hinged connection between the viewport flap 5 and the tubular lateral cover 2. The pair of secondary flap fasteners 7 is mounted onto the tubular lateral cover 2 adjacent to the viewport 4 and is positioned opposite to each other across the viewport 4. This configuration of the fasteners allows the perimeter of the viewport flap, with exception of the hinged connection, to be attached to the lateral cover. In the preferred embodiment the primary flap fastener 6 and the pair of secondary flap fasteners 7 are hook and loop fasteners. In some other embodiments, the primary flap fastener 6 and the pair of secondary flap fasteners 7 include, but is not limited to, buttons, clips, adhesives, or any other suitable method of attachment.

The viewport flap 5, the tubular lateral cover 2, and the base cover 1 of the preferred embodiment are to be made from an opaque, non-woven material. The material is preferred to be opaque such that the contents of the suction canister will not be visible through the present invention when the present invention is properly positioned around the suction canister. A non-woven material is selected in order to provide a bacterial barrier and sterility for anyone handling the suction canister. In an alternate embodiment, show in FIG. 4, the present invention comprises a flap seal 8. The flap seal 8 secures the viewport flap 5 onto the tubular lateral cover 2. The flap seal 8 is perimetrically positioned around the viewport 4. The viewport flap 5 is attached to the tubular lateral cover 2 by the flap seal 8. In the alternate embodiment, the viewport flap 5 is removable attached to the tubular lateral cover 2, allowing the user the choice to cover the viewport 4 for patients or to peel off the viewport flap 5 and leave the viewport 4 uncovered to more easily view volume markers and assess the volume of the fluid within the suction canister.

Although the invention has been explained in relation to its preferred embodiment, it is to be understood that many other possible modifications and variations can be made without departing from the spirit and scope of the invention as hereinafter claimed.

What is claimed is:

1. A suction canister cover comprises:
   a base cover;
   a tubular lateral cover;
   an annular restraint;
   a viewport;
   the tubular lateral cover comprises an annular base edge and a suction canister receiving opening;
   the annular base edge being positioned opposite the suction canister receiving opening along the tubular lateral cover;
   the base cover being perimetrically connected to the annular base edge;
   the annular restraint being mounted onto the tubular lateral cover about the suction canister opening;
   the viewport traversing through the tubular lateral cover between the annular restraint and the cover base; and
   the tubular lateral cover being made of an opaque material.

2. The suction canister cover as claimed in claim 1 comprises:
   a viewport flap; and
   the viewport flap being hingedly connected to the tubular lateral cover, adjacent to the viewport.

3. The suction canister cover as claimed in claim 2 comprises:
   a primary flap fastener;
   a pair of secondary flap fasteners;
   the primary flap fastener being mounted onto the tubular lateral cover adjacent to the viewport;
   the primary flap fastener being positioned opposite to the hinged connection between the viewport flap and the tubular lateral cover;
   the pair of secondary flap fasteners being mounted onto the tubular lateral cover adjacent to the viewport; and
   the pair of secondary flap fasteners being positioned opposite to each other across the viewport.

4. The suction canister cover as claimed in claim 2, wherein the viewport flap is made of an opaque material.

5. The suction canister cover as claimed in claim 2 comprises, wherein the viewport flap is made a non-woven material.

6. The suction canister cover as claimed in claim 1 comprises:
   a viewport flap;
   a flap seal;
   the flap seal being perimetrically positioned around the viewport; and
   the viewport flap being attached to the tubular lateral cover by the flap seal.

7. The suction canister cover as claimed in claim 6, wherein the viewport flap is made of an opaque material.

8. The suction canister cover as claimed in claim 6, wherein the viewport flap is made of a non-woven material.

9. The suction canister cover as claimed in claim 1, wherein the base cover is made of an opaque material.

10. The suction canister cover as claimed in claim 1, wherein the tubular lateral cover and the base cover being made of a non-woven material.

11. A suction canister cover comprises:
    a base cover;
    a tubular lateral cover;
    an annular restraint;
    a viewport;
    the tubular lateral cover comprises an annular base edge and a suction canister receiving opening;
    the annular base edge being positioned opposite the suction canister receiving opening along the tubular lateral cover;
    the base cover being perimetrically connected to the annular base edge;
    the annular restraint being mounted onto the tubular lateral cover about the suction canister opening;
    the viewport traversing through the tubular lateral cover between the annular restraint and the cover base;
    the tubular lateral cover and the base cover being made of an opaque material; and
    the tubular lateral cover and the base cover being made of a non-woven material.

12. The suction canister cover as claimed in claim 10 comprises:
    a viewport flap; and
    the viewport flap being hingedly connected to the tubular lateral cover, adjacent to the viewport.

13. The suction canister cover as claimed in claim 12 comprises:
    a primary flap fastener;
    a pair of secondary flap fasteners;
    the primary flap fastener being mounted onto the tubular lateral cover adjacent to the viewport;
    the primary flap fastener being positioned opposite to the hinged connection between the viewport flap and the tubular lateral cover;
    the pair of secondary flap fasteners being mounted onto the tubular lateral cover adjacent to the viewport; and
    the pair of secondary flap fasteners being positioned opposite to each other across the viewport.

14. The suction canister cover as claimed in claim 12, wherein the viewport flap is made of an opaque material.

15. The suction canister cover as claimed in claim 12 comprises, wherein the viewport flap is made a non-woven material.

16. The suction canister cover as claimed in claim 10 comprises:
    a viewport flap;
    a flap seal;
    the flap seal being perimetrically positioned around the viewport; and
    the viewport flap being attached to the tubular lateral cover by the flap seal.

17. The suction canister cover as claimed in claim 16, wherein the viewport flap is made of an opaque material.

18. The suction canister cover as claimed in claim 16, wherein the viewport flap is made of a non-woven material.

* * * * *